United States Patent [19]

Rockey

[11] Patent Number: 4,501,264
[45] Date of Patent: Feb. 26, 1985

[54] MEDICAL SLEEVE

[76] Inventor: Arthur G. Rockey, 3438 Sharon Rd., Charlotte, N.C. 28211

[21] Appl. No.: 216,989

[22] Filed: Dec. 16, 1980

Related U.S. Application Data

[63] Continuation of Ser. No. 912,010, Jun. 2, 1978, abandoned.

[51] Int. Cl.³ .............................................. A61B 17/00
[52] U.S. Cl. .................................... 128/1 R; 128/344; 604/96; 604/103
[58] Field of Search ............... 128/1 R, 341, 343, 344, 128/348, 349 B, 349 BV, 303 R; 604/96, 103

[56] References Cited

U.S. PATENT DOCUMENTS

| | | | |
|---|---|---|---|
| 3,046,988 | 7/1962 | Moreau et al. | 128/328 |
| 3,863,639 | 2/1975 | Kleaveland et al. | 128/334 R |
| 4,133,315 | 1/1979 | Berman et al. | 128/344 |
| 4,134,405 | 1/1979 | Smit | 128/303 R |
| 4,246,893 | 1/1981 | Berson | 128/1 R |
| 4,416,267 | 11/1983 | Garren et al. | 128/1 R |

Primary Examiner—Ben R. Padgett
Assistant Examiner—T. J. Wallen
Attorney, Agent, or Firm—Pearne, Gordon, Sessions, McCoy, Granger & Tilberry

[57] ABSTRACT

A method and article for medical diagnosis and/or treatment of body disorders, comprising a sleeve unit 10 insertable in a natural body vessel to isolate material flowing into the vessel from direct contact with the interior surface of the vessel. When applied to the treatment of obesity, the sleeve is disposed along a zone in the digestive tract 32 to interfere with the digestive or absorptive function of that zone and thereby reduce net caloric intake.

4 Claims, 9 Drawing Figures

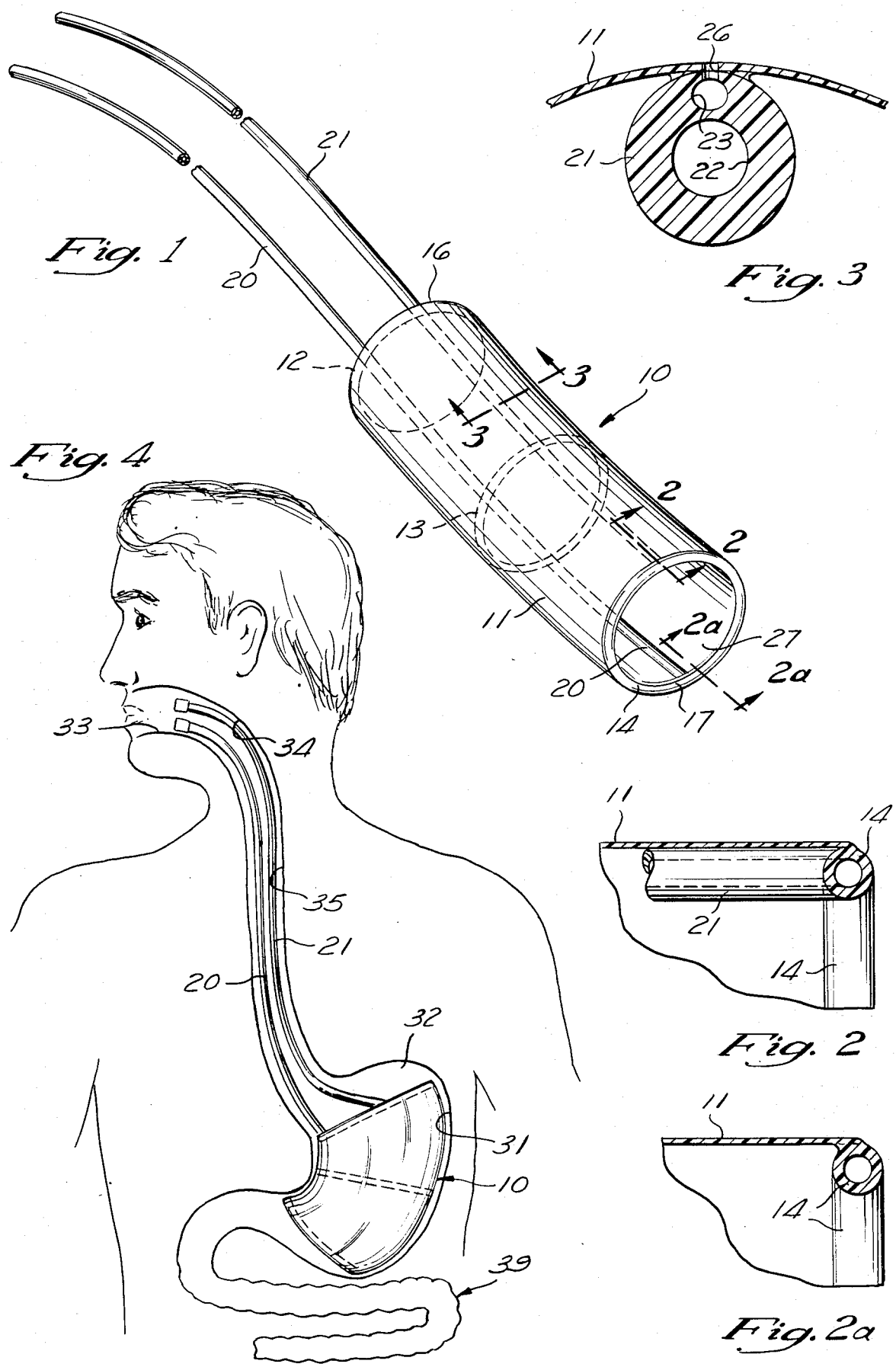

MEDICAL SLEEVE

This is a continuation of application Ser. No. 912,010, filed June 2, 1978, now abandoned.

BACKGROUND OF THE INVENTION

In the diagnosis and/or treatment of disorders of the body, it is known to physically alter the condition or function of hollow viscera or other internal body vessels. Surgical procedures on such vessels include reconstruction of natural tissue, substitution and bypass techniques with natural or artificial implants. Surgery is recognized as always carrying some degree of risk to the patient, both during its actual performance and in postoperative complications or side effects. These risks, of course, are of major concern when the surgery involves the invasion of the great cavity of the trunk of the human body. This is especially true in treatment of such viscera as the heart, liver, or intestines, and in particular when such surgery involves these organs themselves.

In surgical treatment of obesity, for example, the abdominal cavity is exposed to allow reconstruction of the digestive tract, in essence, to reduce the internal surface area available for food digestion or absorption of digested substances. The former technique, a gastric bypass, may be accomplished by anastomosing a minor portion of the stomach to the jejunum while leaving the major portion connected to the duodenum. The latter of these techniques, an intestinal bypass, involves the short-circuiting of a majority of the combined lengths of the jejunum and ileum by connecting the first part of the jejunum to the last part of the ileum.

Both of these operations are deemed to involve such high risk to the patient that they are considered only as a lifesaving undertaking for morbidly obese individuals. Beyond statistically significant operative and overall mortality rates, reported complications following the gastric bypass include marginal ulcers and wound infections. The intestinal bypass involves similar mortality rates and, reportedly, a greater number of postoperative complications and side effects. These include pulmonary emboli, wound infections, gastrointestinal hemorrhage, renal failure, and numerous other disorders. The nature, severity, and frequency of these problems have in fact led to doubts as to the advisability of the techniques for treatment of obesity.

SUMMARY OF THE INVENTION

The invention provides a method and means for isolating the internal walls of hollow viscera or other body vessels from contact with materials, both fluids and solids, occurring naturally, ingested, or otherwise introduced into a body vessel. Isolation of a body vessel, according to the invention, is achieved by positioning and anchoring a sleeve, impervious to materials sought to be isolated within the vessel, in such a manner that the sleeve, at least adjacent its upstream end, is in sealing engagement with the surrounding interior tissue of the vessel. Material otherwise normally flowing into the vessel and being capable of interracting with the vessel to the detriment of the patient's health is thereby contained and rendered ineffectual on or unaffected by the vessel.

An important application of the invention is the non-surgical treatment of obesity through reduction in the effective natural surface area of the digestive tract. In one disclosed embodiment, a sleeve impervious to both gastric secretions and food substances is disposed within the stomach in a manner which prevents contact between these gastric secretions and food substances. More specifically, the sleeve acts as a liner for at least a portion of the internal stomach area while also providing a conduit for food passing through the stomach. The sleeve, which is capable of establishing a circumferential, substantially fluid-tight seal with the walls of the stomach adjacent its upstream end, may be any desired length so that a suitable portion of the internal stomach area is rendered ineffectual in the digestive process. Consequently, the sleeve is operative to limit the efficiency of food absorption in the small intestine.

As disclosed, the sleeve may be introduced into the stomach through the oral cavity and esophagus. In the preferred embodiment, the sleeve is sufficiently flexible to be collapsed into a unit of relatively low bulk for ease of passage through the posterior pharynx and esophagus. Upon reaching a desired position in the stomach, the sleeve is expanded by means carried with the sleeve, including a flexible tube trailing the sleeve. A source of pressurized fluid external of the patient's body is operably connected to the expanding means through this trailing tube to expand the sleeve into sealing engagement with the walls of the stomach. The sleeve may be additionally restrained against further movement along the digestive tract by anchoring the trailing tube or a separate parallel element upstream in the digestive tract.

The tissue isolating function of the disclosed sleeve, in addition to control of the mechanism of digestion, has numerous other applications in diagnosis or treatment of body disorders. For example, the sleeve may be used to chemically and/or physically protect tissue which has been ulcerated, herniated, fissured, or the like from natural body fluids. Ruptured blood vessels or aneurysms may be protected from further damage and allowed to heal by isolating the effect of normal blood pressure from the vessel by containing it within the sleeve.

Stenosis or a sclerotic closing of an artery may be expanded from within by the use of internal compression while still allowing blood to pass through, especially in those individuals whose disease is so far advanced that a graft could not be sutured to the distal portion of the vessel. Still further, where desired, one or more tubes connected to the sleeve may be arranged to provide communication between the annular zone intermediate the protected vessel and the outer surface of the sleeve for introduction of medicines or aspiration of fluids from the zone.

BRIEF DESCRIPTION OF THE DRAWINGS

FIG. 1 is a perspective view of a vessel-insertable medical sleeve unit constructed in accordance with the invention;

FIG. 2 is a fragmentary, cross sectional view on an enlarged scale through the wall of the sleeve unit, taken along the line 2—2 of FIG. 1;

FIG. 2a is a fragmentary, cross sectional view similar to FIG. 3, taken along the line $2_a$—$2_a$ of FIG. 1;

FIG. 3 is a fragmentary, cross sectional view on an enlarged scale, taken along the line 3—3 of FIG. 1 of a trailing filament of the sleeve unit;

FIG. 4 is a schematic illustration of a manner of use of the sleeve to control obesity;

DESCRIPTION OF THE PREFERRED EMBODIMENT

Figure 5:
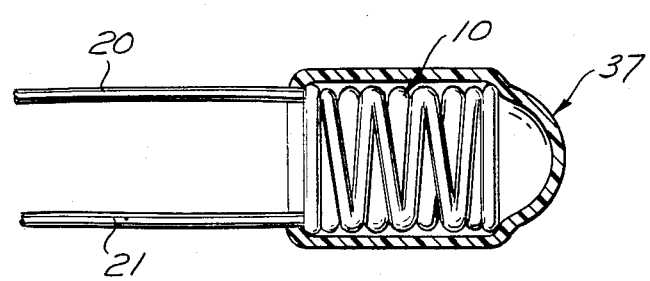
FIG. 5 is a view of the sleeve unit in a compacted condition and contained within a dialator shell for installation.

Referring now to the drawings, and in particular to FIG. 1, there is shown a sleeve unit 10 in the form of a cylindrical, tubular sheath 11 and one or more inflator ring balloons 12-14. The sheath 11 in the illustrated example is a flexible membrane of nontoxic material impervious and chemically resistant to body fluids which it is expected to encounter. The sheath material is selected from a variety of known plastic and/or elastomeric substances. The sheath 11 may be extruded, rolled, or otherwise formed, as desired, into a tube with or without a longitudinal seam or seams.

The inflator ring balloons 12-14 as indicated in FIG. 1 are flexible, hollow, torroid-like elements spaced axially along the interior of the sheath 11. As indicated, the rings 12 and 14 are adjacent opposite ends 16 and 17 of the sheath 11. The ring balloons 12-14 may be formed of a material the same as or like that of the sheath 11, and are either integrally formed thereon or are bonded thereto by heat, adhesive, solvent or like means. While the sheath 11 is illustrated as a cylinder, it will be understood that it may take other configurations, such as a frustum or a sphere truncated adjacent opposite poles, or a tubular elbow of constant or varying diameter. The sleeve unit 10 includes at least one, and preferably two, trailing hollow filaments 20,21 connected thereto by bonding or other suitable means. These filaments 20,21 may be made of the same or similar material as the sheath 11. In the illustrated case, each of the filaments 20-21 includes a central lumen 22 and an auxiliary lumen 23. When desired or necessary, additional lumens may be disposed in the wall of each filament 20-21. Ideally, one of the filaments 20 has its central lumen 22 in fluid communication with an upstream one 12 of the ring balloons, while the other filament 21 has its central lumen 22 in fluid communication with the remaining ring balloons 13 and 14.

As suggested in FIG. 3, longitudinally spaced, generally radial passages 26 provide communication from the auxiliary lumens 23 of each filament 20, 21 through the adjacent wall of the sheath 11 to points external of the sleeve unit 10. The exterior surface of the filaments 20,21 and internal surface of the sheath 11 are sealed to one another by suitable means, such as bonding or the like, at their points of tangency so that fluids in the auxiliary lumens cannot escape into the interior, designated 27, of the sheath 11 at the radial passages or apertures 26.

Figure 6:
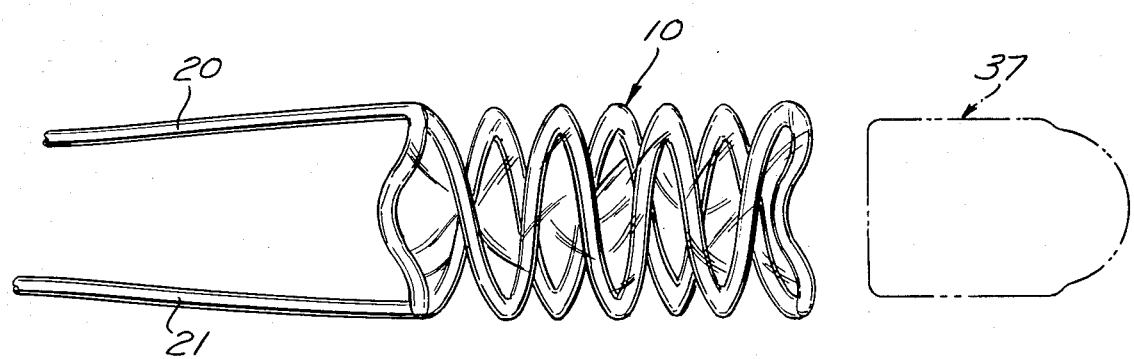
FIG. 6 is a view of the sleeve unit depicting an intermediate configuration in a progressive sequence of expansion from the condition of FIG. 4.

The sleeve unit 10 is implanted in a body vessel in order to isolate the walls of such vessel from fluids normally flowing into it. FIG. 4 illustrates a manner of use of the sleeve unit 10 to isolate the internal surface area or lumen, designated 31, of a human stomach 32 and its secretions from food substances passing through it. The sleeve unit 10 is implanted in the stomach 32 in a nonsurgical manner by passing it through an oral cavity 33, pharynx 34, and esophagus 35. To facilitate introduction of the sleeve unit 10 into the stomach 32, the sleeve unit is folded on itself accordion fashion to reduce its length and diameter. In its folded or compacted state, the sleeve unit 10 is contained within a dialator shell or cup 37 (FIGS. 5 and 6). The dialator shell 37 has a rounded profile for ease of passage through the natural lumen of the digestive tract, generally indicated at 39 (FIG. 4). The dialator shell 37 carrying the collapsed sleeve unit 10 is inserted through the epiglotis, whereupon natural swallowing action allows it to be readily advanced into the stomach 32.

Figure 7:
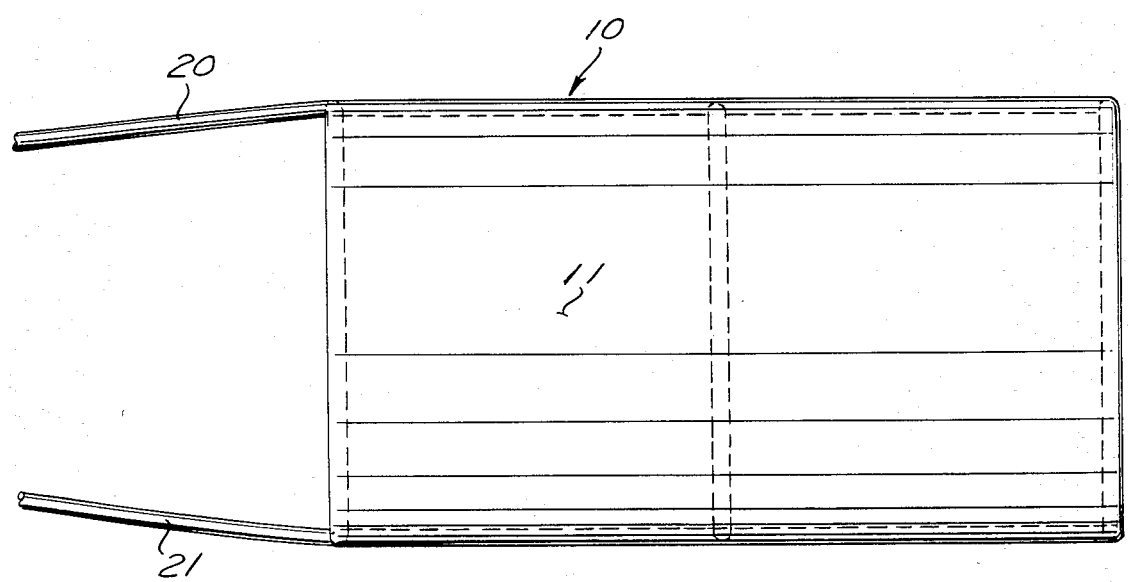
FIG. 7 is a view of the sleeve progressed in its transition from FIG. 5 through FIG. 6 to a fully expanded configuration essentially corresponding to FIG. 4.

Upon reaching the stomach 32, one or both of the central lumens 22 of the filaments 20,21 are connected to a source of pressurized fluid, such as air, ordinarily external of the oral cavity 33. Lower sections of the filaments 20, 21 longitudinally associated with the sheath 11 develop forces upon pressurization, tending to unfold themselves along with the sheath. FIG. 6 depicts this action, wherein the dialator shell 37 is released from the sleeve unit 10 and allowed to pass through the lower portion of the digestive tract 39. The sleeve unit 10 in a continuous sequence of movement expands from the intermediate position of FIG. 6 to that of FIG. 7.

The final position of the sleeve unit 10 in the stomach 32 may be adjusted by pumping fluid through the auxiliary lumens 23 in such a manner that it issues from the passages 26 as a jet developing a reaction force to shift the adjacent area of the sleeve unit in one direction or another, depending on the orientation of the passages. These passages 26 may be provided with either an axial or tangential component in their orientation with respect to the axial direction of the sleeve to cause corresponding axial or turning movement of the sleeve. Preferably, the sleeve unit 10, including the filaments 20, 21 and ring balloons 12-14, is provided with sufficient radiopaque material to permit external observation of its position and configuration. When the position of the sleeve unit 10 is satisfactory, the ring balloons 12-14 are finally inflated through the central filament lumens 22, again by a source of pressurized fluid external of the patient's body. Inflation of the ring balloons 12-14 causes them, in the manner of circumferential stiffening ribs, to fully expand the sleeve into tight sealing engagement with the interior surface 31 of the stomach vessel 32. The ends of the filaments 20,21 distal from the sleeve unit 10 are anchored to a posterior tooth or prosthesis by suitable fastening means or are sutured in place. The central or main lumens 22 of the filaments 20,21 are closed at these anchoring points by heat sealing, plugging, or the like, to indefinitely maintain a pressurized state in the connected ring balloons 12-14 to keep the adjacent sleeve areas in fluid-tight engagement with the stomach wall 31. Where desired, for example, to release fluids secreted by the stomach walls 31, the middle and lower ring balloons 13, 14 may be intermittently or permanently depressurized so that these fluids may pass through the remainder of the digestive tract. Alternatively, fluids secreted by the stomach area 31 shielded by the sleeve unit 10 may be aspirated through the oral cavity by way of the auxiliary lumens 23 and passages 26. Moreover, if desired, medicine may be carried into the annular zone defined between the sheath 11 and stomach walls 31 through the oral cavity by way of the auxiliary lumens 23 and passages 26.

The sleeve unit 10, by isolating the walls 31 of the stomach 32 from ingested food passing through it, reduces the digestive efficiency of the stomach. This results from interference with the normal contact of gastric juices, secreted by the stomach walls 31, on such food and the inability of the intestines of the lower digestive tract to absorb undigested food. Thus, the patient, while consuming food in even large quantities, is enabled to lose weight, since only a limited amount of the ingested food is ultimately absorbed.

Various other uses of the disclosed sleeve 10 or its equivalents are contemplated in the treatment of body disorders. For instance, the sleeve 10 may be disposed in the small intestine, rather than in the stomach, to directly reduce the effective area of the intestine available for absorption, again for the control of obesity. When disposed in the stomach, the sleeve may be utilized to medicate an ulcerous zone and isolate it from gastric juices to hasten normal recovery.

Figure 8:
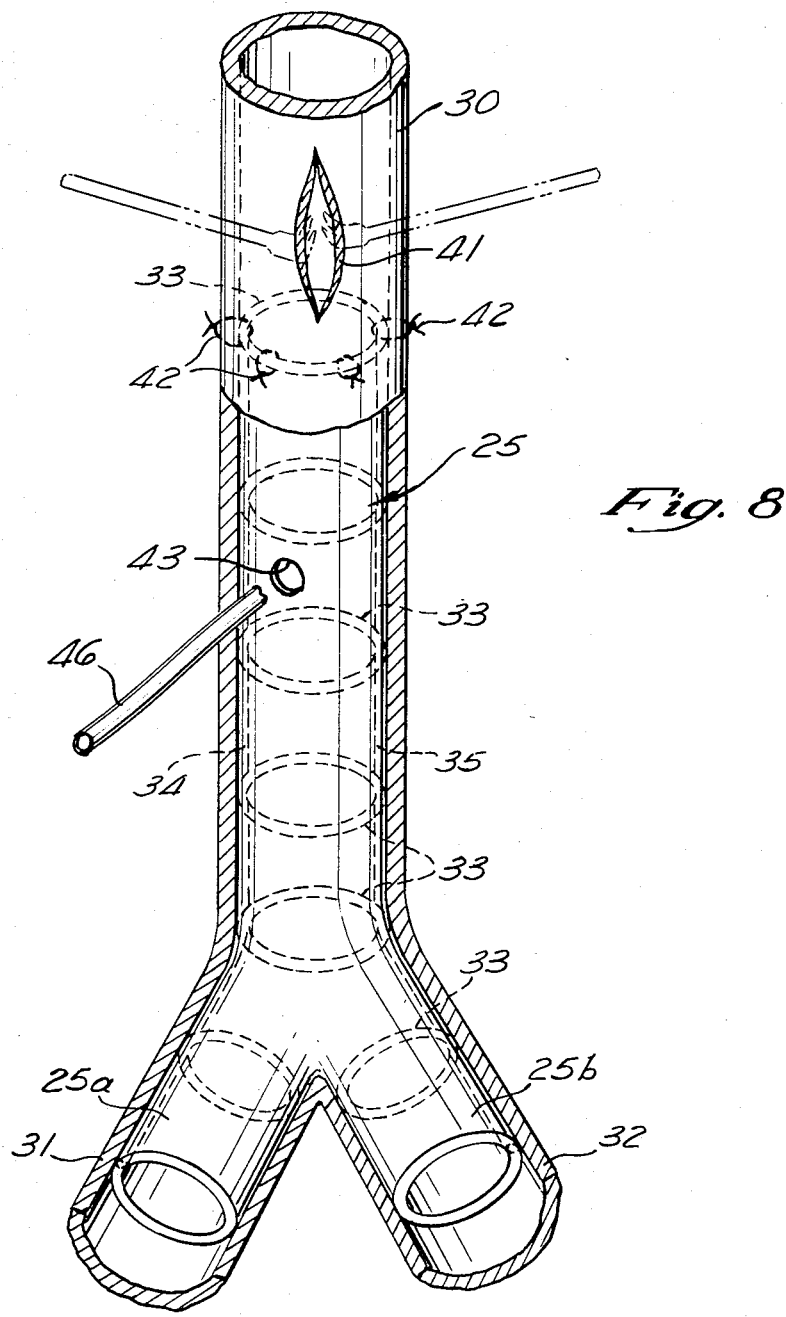
FIG. 8 is a schematic view of a second embodiment of the sleeve of the invention employed within an aorta.

Referring now to FIG. 8, there is shown a second embodiment of the invention wherein a sleeve 25 is disposed within a human aorta 30 and associated right and left common iliac arteries 31, 32. The sleeve 25 is bifurcated at one end to provide a pair of branches 25a and 25b corresponding to the right and left common iliac arteries 31, 32 respectively. The sleeve 25 has a construction essentially the same as the earlier-described sleeve 10. Ring balloons 33 are spaced axially along the sleeve including the branch portions 25a,25b. Each of the ring balloons 33 is in fluid communication with at least one hollow filament 34,35 for purposes of inflation.

The sleeve 25 is advantageously employed in cases of advanced blood vessel disease where a patient's tissue is such that it is impossible to sew or anastomose it with grafts or artificial vessels. An incision 41 is made in the vessel 30 to allow the positioning of the sleeve 25 therein. The sleeve 25 is expanded into position by directing fluid pressure into the elongated filaments 34,35 in any suitable manner such as disclosed above with use of free extensions (not shown) of these filaments.

The sleeve 25 is anchored in the vessel 30, for example, by sutures 42 near the incision 41, while the distal portion of the sleeve remains free. One or more holes 43 may be cut into the wall of the sleeve prior to placement within the vessel to provide blood flow to various arterial branches 46. The sleeve 25 is preferably formed of relatively inelastic material or otherwise is circumferentially reinforced with inelastic material along its length so that the pressure of blood flowing through the sleeve is effectively isolated from the vessel 30.

The invention is not restricted to the slavish imitation of each and every detail set forth above. Obviously, devices may be provided which change, eliminate, or add certain specific details without departing from the scope of the invention.

What is claimed is:

1. A method of controlling obesity, comprising the steps of positioning a sleeve impervious to digestive juices and normal foods in the digestive tract, arranging the sleeve in the digestive tract in such a manner that substantially all normally ingested food material passing naturally through the oral cavity and then passing through the digestive tract is caused to pass through the sleeve while being isolated from direct contact with the surrounding area of the interior walls of the digestive tract and body fluids secreted by such surrounding area interior walls such that natural absorption of food material in the digestive tract is impaired and a net caloric intake for a given quantity of ingested food is thereby reduced, said sleeve being disposed substantially entirely in the stomach.

2. A method of controlling obesity, comprising the steps of positioning a sleeve impervious to digestive juices and normal foods in the digestive tract, arranging the sleeve in the digestive tract in such a manner that substantially all normally ingested food material passing naturally through the oral cavity and then passing through the digestive tract is caused to pass through the sleeve while being isolated from direct contact with the surrounding area of the interior walls of the digestive tract and body fluids secreted by such surrounding area interior walls such that natural absorption of food material in the digestive tract is impaired and a net caloric intake for a given quantity of ingested food is thereby reduced, said sleeve being anchored in position in said digestive tract by means extending through the digestive tract to the oral cavity.

3. A method as set forth in claim 2, wherein said sleeve is positioned in said digestive tract through the oral cavity.

4. A method of controlling obesity, comprising the steps of positioning a sleeve impervious to digestive juices and normal foods in the digestive tract, arranging the sleeve in the digestive tract in such a manner that substantially all normally ingested food material passing naturally through the oral cavity and then passing through the digestive tract is caused to pass through the sleeve while being isolated from direct contact with the surrounding area of the interior walls of the digestive tract and body fluids secreted by such surrounding area interior walls such that natural absorption of food material in the digestive tract is impaired and a net caloric intake for a given quantity of ingested food is thereby reduced, said sleeve being passed through the oral cavity and other upper areas of the digestive tract in a compacted condition and being expanded along substantially its full axial length into sealing contact with at least a portion of said surrounding area of said interior walls.

* * * * *